(12) United States Patent
de los Rios et al.

(10) Patent No.: US 12,295,954 B2
(45) Date of Patent: May 13, 2025

(54) METHODS OF TREATING FIBROSIS

(71) Applicant: Endeavor Biomedicines, Inc., San Diego, CA (US)

(72) Inventors: Miguel de los Rios, Del Mar, CA (US); John Hood, Del Mar, CA (US); Anita Difrancesco, San Diego, CA (US); Luis A. Dellamary, San Marcos, CA (US)

(73) Assignee: Endeavor BioMedicines, Inc., San Diego, CA (US)

( * ) Notice: Subject to any disclaimer, the term of this patent is extended or adjusted under 35 U.S.C. 154(b) by 109 days.

(21) Appl. No.: 18/115,593

(22) Filed: Feb. 28, 2023

(65) Prior Publication Data

US 2023/0201195 A1  Jun. 29, 2023

Related U.S. Application Data

(63) Continuation of application No. 17/735,798, filed on May 3, 2022, now Pat. No. 11,628,167, which is a continuation of application No. PCT/US2021/054713, filed on Oct. 13, 2021.

(60) Provisional application No. 63/091,128, filed on Oct. 13, 2020.

(51) Int. Cl.
*A61K 31/502* (2006.01)
*A61P 11/00* (2006.01)

(52) U.S. Cl.
CPC ............ *A61K 31/502* (2013.01); *A61P 11/00* (2018.01)

(58) Field of Classification Search
CPC .................................................... A61K 31/502
See application file for complete search history.

(56) References Cited

U.S. PATENT DOCUMENTS

| | | | |
|---|---|---|---|
| 4,289,772 A | 9/1981 | Campbell et al. | |
| 7,981,892 B2 | 7/2011 | Hipskind et al. | |
| 8,273,742 B2 | 9/2012 | Hipskind et al. | |
| 9,000,023 B2 | 4/2015 | Hipskind et al. | |
| 11,154,541 B2 | 10/2021 | Xie | |
| 11,628,167 B2 * | 4/2023 | de los Rios .......... | A61K 31/502 514/248 |
| 2010/0324048 A1 | 12/2010 | Hipskind et al. | |
| 2011/0183948 A1 | 7/2011 | Levine et al. | |
| 2011/0301162 A1 | 12/2011 | Deak et al. | |
| 2016/0341726 A1 | 11/2016 | Humphreys et al. | |
| 2018/0256570 A1 | 9/2018 | Peterson et al. | |
| 2019/0255042 A1 | 8/2019 | Cai et al. | |
| 2020/0000784 A1 | 1/2020 | Xie | |
| 2021/0315871 A1 | 10/2021 | Xie | |
| 2022/0354832 A1 | 11/2022 | Xie | |
| 2023/0201195 A1 | 6/2023 | de Los Rios et al. | |
| 2023/0201196 A1 | 6/2023 | de los Rios et al. | |
| 2024/0342170 A1 | 10/2024 | de Los Rios et al. | |

FOREIGN PATENT DOCUMENTS

| | | |
|---|---|---|
| GB | 2528298 A | 1/2016 |
| WO | WO-9726258 A1 | 7/1997 |
| WO | WO-99/52534 A1 | 10/1999 |
| WO | WO-00/74706 A1 | 12/2000 |
| WO | WO-2003/088970 A2 | 10/2003 |
| WO | WO-04/020599 A2 | 3/2004 |
| WO | WO-2005/033288 A2 | 4/2005 |
| WO | WO-2005/080378 A1 | 9/2005 |
| WO | WO-2006/004589 A2 | 1/2006 |
| WO | WO-2006/028958 A2 | 3/2006 |
| WO | WO-2008/028689 A1 | 3/2008 |
| WO | WO-2008/110611 A1 | 9/2008 |
| WO | WO-2009/002469 A1 | 12/2008 |
| WO | WO-2009/035568 A1 | 3/2009 |
| WO | WO-2009/134574 A2 | 11/2009 |
| WO | WO-2010/007120 A1 | 1/2010 |
| WO | WO-2010/056588 A1 | 5/2010 |
| WO | WO-2010/056620 A1 | 5/2010 |
| WO | WO-2010/062507 A1 | 6/2010 |
| WO | WO-2010/147917 A1 | 12/2010 |
| WO | WO-2014/191736 A1 | 12/2014 |
| WO | WO-2017/095757 A1 | 6/2017 |
| WO | WO-2020/018904 A1 | 1/2020 |
| WO | WO-2022/081661 A1 | 4/2022 |
| WO | WO-2024/182483 A1 | 9/2024 |

OTHER PUBLICATIONS

International Search Report and Written Opinion mailed Mar. 24, 2022 for International Application Serial No. PCT/US2021/054713 filed on Oct. 13, 2021.
Wang et al., "Synthesis and evaluation of novel dimethylpyridazine derivatives as hedgehog signaling pathway inhibitors," Bioorganic & Medicinal Chemistry, 2018, 26(12), pp. 3308-3320.
Hu et al., "An Overview of Hedgehog Signaling in Fibrosis," Molecular Phamacology, 2015, 87(2), pp. 174-182.
Hu et al., "Reemergence of Hedgehog Mediates Epithelial-Mesenchymal Crosstalk in Pulmonary Fibrosis," American Journal of Respiratory Cell and Molecular Biology, 2015, vol. 52(4), pp. 418-428.
Wang et al., "CASREACT 169: 165515," 2018.
Bendell, J. et al., A Phase I Dose-Escalation, Pharmacokinetic (PK) and Pharmacodynamic (PD) Evaluation of LY2940680, an Oral Smoothened (Smo) Inhibitor/Poster, 24th European Cancer Organization (ECCO) EORTC-NCI-AACR Symposium on Molecular Targets and Cancer Therapeutics. Dublin, Ireland, 2012.
Bendell, J. et al., Phase I Study of LY2940680, a Smo Antagonist, in Patients with Advanced Cancer Including Treatment-Naive and Previously Treated Basal Cell Carcinoma, Clinical Cancer Research, 24(9):2082-2091 (2019).
Bender, M. et al., Abstract 2819: Identification and Characterization of a Novel Smoothened Antagonist for the Treatment of Cancer with Deregulated Hedgehog Signaling. Presented at the AACR 102nd Annual Meeting. Orlando, FL, 2011.

(Continued)

*Primary Examiner* — Rei Tsang Shiao
(74) *Attorney, Agent, or Firm* — Choate, Hall & Stewart LLP

(57) ABSTRACT

The present specification provides methods and compositions for treating fibrosis, particularly pulmonary fibrosis. The pulmonary fibrosis may be idiopathic or arise following an infection of the lung. The lung infection can be by SARS-CoV-2. Lung function stabilizes or is improved as a result of treatment.

13 Claims, 4 Drawing Sheets

(56) References Cited

OTHER PUBLICATIONS

Bhowmick, N. et al., TGF-beta signaling in fibroblasts modulates the oncogenic potential of adjacen epithelia, Science, 303(5659):848-851 (2004).
Bonow, R. et al., Population-wide trends in aortic stenosis incidence and outcomes, Circulation, 131 (11):969-971 (2015).
Boudoulas, K. et al., Etiology of valvular heart disease in the 21st century, Cardiology, 126:139-152 (2013).
Casaclang-Verzosa, G et al., Echocardiographic Approaches and Protocols for Comprehensive Phenotypic Characterization of Valvular Heart Disease in Mice, J Vis Exp., 14(120):54110 (2017).
Chu, Y. et al., Fibrolic Aortic Valve Stenosis in Hypercholesterolemic/ Hypertensive Mice, Arterioscler Thromb Vase Biol., 36(3):466-474 (2016).
Coffey, S. et al., The prevalence, incidence, progression, and risks of aortic valve sclerosis: a systematic review and meta-analysis, J Am Coll Cardiol, 63(25 Pt A):2852-2861 (2014).
Damen, FW. et al., High-Frequency 4-Dimensional Ultrasound (4DUS): A Reliable Method for Assessing Murine Cardiac Function, Tomography, 3(4):180-187 (2017).
Dummer, R. et al., The 12-month analysis from Basal Cell Carcinoma Outcomes with LDE225 Treatment (Bolt): A phase 11, randomized, double-blind study of sonidegib in patients with advanced basal cell 15 carcinoma, J Am Acad Dermatol., 75(1):113-125 e115 (2016).
Dweck, M. R. et al., Calcific aortic stenosis: a disease of the valve and the myocardium, Journal of the American College of Cardiology., 60(19): 1854-1863 (2012).
Edeling, M. et al., Developmental signalling pathways in renal fibrosis: the roles of Notch, Wnt and Hedgehog, Nav Rev Nephrol., 12(7):426-439 (2016).
Faggiano, P. et al., Epidemiology and cardiovascular risk factors of aortic stenosis, Cardiovasc Ultrasound, 4:27 (2006).
Frank-Kamenetsky, M., et al., Small-molecular modulators of Hedgehog signaling: identification and characterization of Smoothened agonists and antagonists, Journal of Biolology 1(2):1-10 (2002).
Gao, Z. et al., Effect of mutations on drug resistance of smoothened receptor toward inhibitors probed by molecular modeling, Elsevier, 741 (2020).
Hirsova, P. et al., Vismodegib suppresses TRAIL-mediated liver injury in a mouse model of nonalcoholic steatohepatitis, PLOS One, 8(7): e70599 (2013).
International Search Report for ISR/WO PCT/US2010/038568, 4 pages (mailed Jul. 28, 2010).
Jacobsen, A. et al., Hedgehog Pathway Inhibitor Therapy for Locally Advanced and Metastatic Basal Cell Carcinoma: A Systematic Review and Pooled Analysis of Interventional Studies, JAMA Dermatol., 152(7):816-824 (2016).
Jia, Y., The Hedgehog pathway: role in cell differentiation, polarity and proliferation, Arch Toxicol., 89(2):179-191 (2015).
Lam, CW et al., A frequent activated smoothened mutation in sporadic basal cell carcinomas, Oncogene, 18(3):833-836 (1999).
Lear, J. T., Oral hedgehog-pathway inhibitors for basal-cell carcinoma, N Engl J Med, 366(23):2225-6 (2012).
Lee, J., et al., A small-molecule antagonist of the Hedgehog signaling pathway, ChemBioChem, 8(2016):1916-1919 (2007).

Maher, T. M. et al., ENV-101, a Novel Hedgehog Inhibitor, Increases Lung Function and Reduces Lung Fibrosis in Patients with Idiopathic Pulmonary Fibrosis: Results from a m Randomized, Double-blind, Placebo-controlled Phase 2 Trial, oral presentation at ATS 2024, San Diego, CA on May 19, 2024.
Maher, T. M. et al., ENV-101, a Novel Hedgehog Inhibitor, Increases Lung Function and Reduces Lung Fibrosis in Patients with Idiopathic Pulmonary Fibrosis: Results from a Randomized, Double-blind, Placebo-controlled Phase 2 Trial, presented at ATS 2024, San Diego, CA on May 19, 2024.
Maher, T. M. et al., ENV-101, A Novel Hedgehog Inhibitor, Increases Lung Function, and Reduces Lung Fibrosis in Patients With Idiopathic Pulmonary Fibrosis: Results From a Randomized, Double-blind, Placebo-controlled Phase 2 Trial, Am J. Respir Crit., 209:A1056 (2024).
Mao, J. et al., A novel somatic mouse model to survey tumorigenic potential applied to the Hedgehog pathway, Cancer Res., 66(20):10171-10178 (2006).
McMahon, G., VEGF Receptor Signaling in Tumor Angiogenisis, The Oncologist, 5(suppl 1):3-10 (2000).
Moshai, E. et al., Targeting the hedgehog-glioma-associated oncogene homolog pathway inhibits bleomycin-induced lung fibrosis in mice, Am J Respir Cell Mol Bio., 51(1): 11-25 (2014).
Noble, P. W. et al., Pulmonary fibrosis: patterns and perpetrators, Journal of Clinical Investigation. 122(8): 2756-2762) (2012).
Pinedo, et al., Translational Research: The Role of VEGF in Tumor Angiogenesis, The Oncologist, 5(suppl 1):1-2 (2000).
Rudin, C. et al., Treatment of Medulloblastoma with Hedgehog Pathway Inhibitor GDC-0449, N Engl. J Med., 361:12 (2009).
Sekulic, A. et al., Efficacy and Safety of Vismodegib in Advanced Basal-Cell Carcinoma, N. Engl. J. Med., 366(23): 2171-2179 (2012).
Sekulic, A. et al., Long-term safety and efficacy of vismodegib in patients with advanced basal cell carcinoma: final update of the pivotal Erivance BCC study, BMC Cancer, 17(1):332 (2017).
Stewart, G. et al., Expression of the developmental Sonic hedgehog (Shh) signalling pathway is up-regulated in chronic lung fibrosis and the Shh receptor patched 1 is present in circulating T lymphocytes, J Pathol., 199:488-495 (2003).
Tremblay, M., et al., Recent patents for Hedgehog pathway inhibitors for the treatment of malignancy, Expert Opin. Ther. Patents, 19(8):1039-1056 (2009).
Tremblay, M., et al., Semisynthetic cyclopamine analogues as potent and orally bioavailable Hedgehog pathway antagonists, J. Med. Chem., 51: 6646-6649 (2008).
Ueno, H. et al., A phase I and pharmacokinetic study of taladegib, a Smoothened inhibitor, in Japanese patients with advanced solid tumors, Investigational New Drugs, 1-10 (2017).
Wikipedia, HEK 293 cells, http://en.wikipedia.org/wiki/HEK_293_cells, last modified on Jun. 3, 2014 and downloaded on Jul. 15, 2014.
Wilson, M. S. et al., Pulmonary fibrosis: pathogenesis, etiology and regulation, Mucosal Immunology, 2(2): 103-121 (2009).
Written Opinion for ISR/WO PCT/US2010/038568, 5 pages (mailed Jul. 28, 2010).
Xie, J. et al., Activating Smoothened mutations in sporadic basal-cell carcinoma, Nature, 391(6662):90-92 (1998).
Yang, L. et al., Identification of signature genes for detecting hedgehog pathway activation in esophageal cancer, Pathol. Oncol. Res., 17:387-391 (2011).

\* cited by examiner

METHODS OF TREATING FIBROSIS

CROSS-REFERENCE TO RELATED APPLICATIONS

This application is a continuation of U.S. patent application Ser. No. 17/735,798, filed May 3, 2022, which is a continuation of PCT/US2021/054713, filed Oct. 13, 2021, which claims the benefit of, and priority to, U.S. Provisional Patent Application Ser. No. 63/091,128, filed Oct. 13, 2020, the entire contents of each of which are incorporated by reference herein.

BACKGROUND

The treatment of fibrotic diseases has proved challenging. Although there are approved drugs of the treatment of some fibrotic diseases, such as pirfenidone and nintedanib for idiopathic pulmonary fibrosis (IPF). However, these drugs only modestly slow progression of the disease, but do not stop or reverse it. The Hedgehog/GLI signaling pathway is an important regulator of normal embryonic development and had been implicated in the development of fibrosis as well. However, inhibition of the canonical Hh signaling pathway, for example by inhibiting Smoothened (SMO), a G protein-couple receptor in the Hedgehog (Hh) signaling pathway, has failed to lead to a clinically viable treatment for pulmonary fibrosis, kidney fibrosis, or myelofibrosis. Indeed, cyclopamine and IPI-926, inhibitors of SMO have been found to be ineffective in treating kidney fibrosis. Additionally, a phase 2 clinical trial of IPI-926 in myelofibrosis did not support continued development. A phase 1b clinical trial of another SMO inhibitor, vismodegib (in combination with pirfenidone) for the treatment of IPF suggested some degree of efficacy, but many patients dropped out of the study because they could not tolerate the drug and development of the drug for this indication was abandoned.

SUMMARY

Disclosed herein are methods and compositions for treating fibrotic disease using inhibitors of the hedgehog signaling pathway that are sufficiently potent and tolerable to admit of clinical utilization.

One aspect is a method of treating fibrosis comprising administering an inhibitor of Gli1. Inhibition of Gli1 can be indirect. In some embodiments, an inhibitor of SMO is used to indirectly inhibit Gli1.

One aspect is a method of treating fibrosis comprising administering means for inhibiting Gli1. Inhibition of Gli1 can be indirect. In some embodiments, means for inhibiting SMO are used to indirectly inhibit Gli1. In various embodiments, one or another genus or species of SMO inhibitor is specifically excluded.

With respect to the above aspects, in some embodiments, the inhibitor of Gli1 or the means for inhibiting Gli1 is an inhibitor of SMO (or means for inhibiting SMO). In some embodiments, the inhibitor of SMO, the inhibitor of Gli1, or the means for inhibiting Gli1 or SMO is a compound of Formula I:

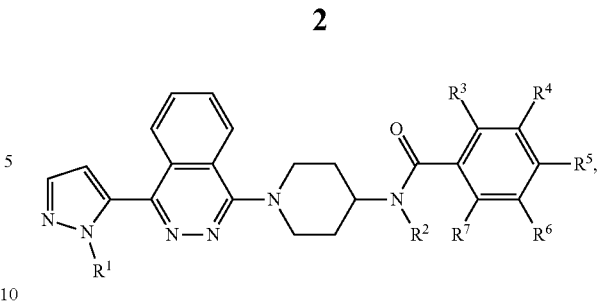

wherein, $R^1$ is hydrogen or methyl; $R^2$ is hydrogen or methyl; $R^3$, $R^4$, $R^5$, $R^6$, or $R^7$ are independently hydrogen, fluoro, chloro, cyano, trifluoromethyl, trifluoromethoxy, difluoromethoxy, methylsulfonyl, or trifluoromethylsulfonyl, provided that at least three of $R^3$, $R^4$, $R^5$, $R^6$, and $R^7$ are hydrogen; or a pharmaceutically acceptable salt thereof. Under standard nomenclature used throughout this disclosure, the terminal portion of the designated side chain is described first, followed by the adjacent functionality toward the point of attachment. For example, a methylsulfonyl substituent is equivalent to $CH_3$—$SO_2$—. In some embodiments, the compound of Formula I is 4-Fluoro-N-methyl-N-(1-(4-(1-methyl-1H-pyrazol-5-yl)phthalazin-1-yl)piperidin-4-yl)-2-(trifluoromethyl)benzamide (CAS 1258861-20-9):

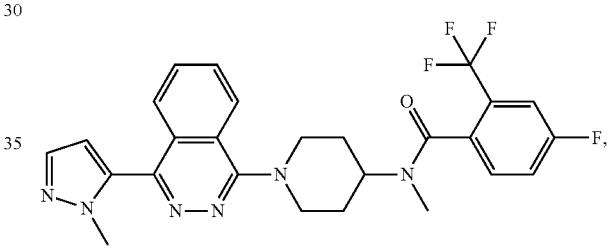

also known as taladegib.

With respect to the above aspects, in some embodiments, the inhibitor of SMO, the inhibitor of Gli1, or the means for inhibiting Gli1 or SMO is a compound of Formula II:

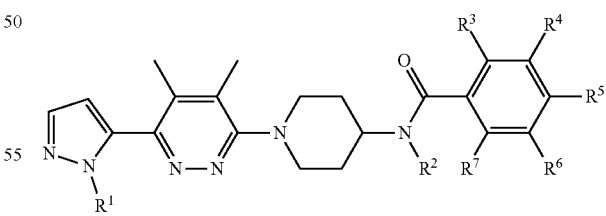

wherein, $R^1$ is hydrogen or methyl; $R^2$ is hydrogen or methyl; $R^3$, $R^4$, $R^5$, $R^6$, or $R^7$ are independently hydrogen, fluoro, chloro, cyano, trifluoromethyl, trifluoromethoxy, difluoromethoxy, methylsulfonyl, or trifluoromethylsulfonyl, provided that at least three of $R^3$, $R^4$, $R^5$, $R^6$, and $R^7$ are hydrogen; or a pharmaceutically acceptable salt thereof. In some embodiments, the compound of Formula II is compound L-4, having the structure

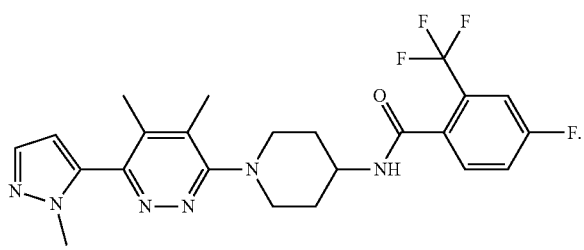 [SMILES: Cc1c(-c2ccnn2C)nnc(N2CCC(NC(=O)c3ccc(F)cc3C(F)(F)F)CC2)c1C]

With respect to the above aspects, in some embodiments, the inhibitor of Gli1 or the means for inhibiting Gli1 is administered to a patient in need thereof, that is, a patient having a fibrotic disease. In some embodiments, the fibrotic disease is idiopathic pulmonary fibrosis (IPF). In some embodiments, the fibrotic disease is pulmonary fibrosis following infection, including a bacterial or viral infection. In most instances, the fibrosis develops after years-long chronic infections so that the role of the infection in causing the fibrosis cannot be conclusively demonstrated; such fibrosis is therefore still classified as idiopathic. Covid-19 provides a counterpoint, in that onset of fibrosis can be very rapid. In some embodiments, the pulmonary fibrosis follows infection with SARS-CoV-2. In some embodiments, the fibrotic disease is scleroderma. In some instances, the fibrotic disease is systemic scleroderma (also known as systemic sclerosis) and in further instances, systemic scleroderma involving the lung. In some embodiments, the fibrotic disease is liver fibrosis, such as in non-alcoholic steatohepatitis (NASH). In some embodiments, the fibrotic disease is kidney fibrosis. In some embodiments, the fibrotic disease is gastric fibrosis. In some embodiments, the patient is a human.

With respect to the above aspects, in some embodiments, the inhibitor of Gli1 or the means for inhibiting Gli1 is administered in an effective amount. In some embodiments, the effective amount is effective for reducing symptoms. In some embodiments, the effective amount is effective for slowing or halting progression of the disease. In some embodiments, the effective amount is effective for reducing impairment due to the disease. In some embodiments, the effective amount is effective for reversing impairment due to the disease (causing improvement). With respect to IPF, impairment can be measured as changes in lung function, for example, as determined by spirometry. Spirometry measures that can be used include forced vital capacity (FVC), forced expiratory volume in 1 second ($FEV_1$), and diffusion capacity of the lungs for carbon monoxide ($DL_{CO}$). The extent of fibrosis can also be assessed by imaging, such as high resolution computed tomography (HRCT). In some embodiments, the effective amount comprises 50-200 mg of the inhibitor of Gli1 or the means for inhibiting Gli1.

One aspect is a pharmaceutical compound comprising the inhibitor of Gli1 or the means for inhibiting Gli1. In some embodiments, the inhibitor of Gli1 or the means for inhibiting Gli1 is a compound of Formula 1 or a pharmaceutically acceptable salt thereof. In some embodiment the compound of Formula 1 is taladegib.

BRIEF DESCRIPTION OF DRAWINGS

FIG. 4A presents representative images of anti-α-SMA immunostained lung sections from sham control, vehicle-treated, and taldegib-treated mice. FIG. 4B depicts the percent α-SMA positive area from the individual mice and the mean and standard deviation for the treatment groups.

DESCRIPTION

Figure 1:
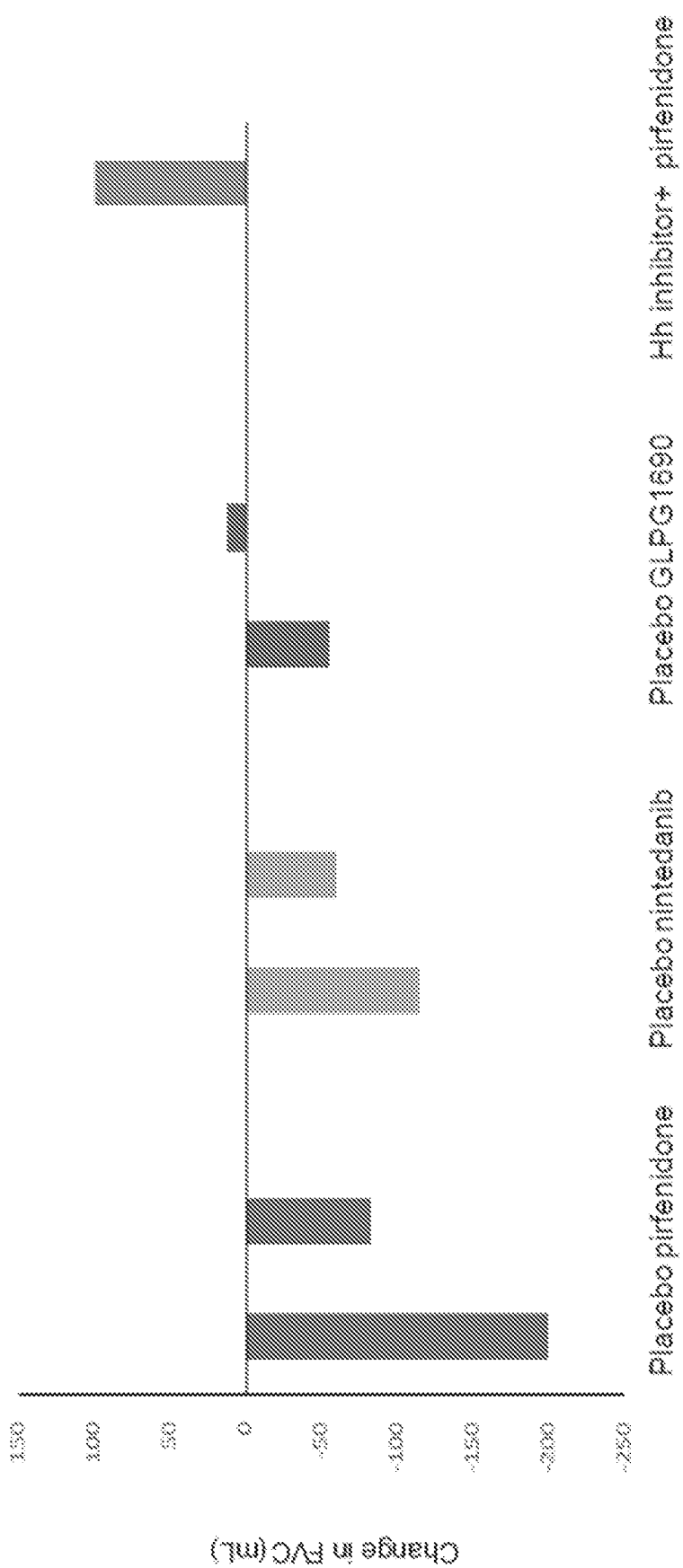
FIG. 1 depicts a comparison of clinical trial results for four IPF treatments: pirfenidone, nintedanib, GLPG1690, and the Hh inhibitor, vismodegib. The trials for pirfenidone, nintedanib, GLPG1690 were placebo controlled, while the vismodegib trial was open label. The pirfenidone data is the mean of three phase 3 studies at 24 weeks. The nintedanib data is the mean of two phase 3 studies at 24 weeks. The GLPG1690 data is phase 1b data at 12 weeks. The Hh inhibitor (vismodegib) data is phase 1b data as 24 weeks.

The general mechanism of fibrotic disease has been understood to involve an initial tissue insult causing an upregulation of hedgehog, driving transdifferentiation of cells into myofibroblasts (that is, the conversion of differentiated cells (non-stem cells) into another type of differentiated cell, in this case myofibroblasts). The physiologic function of myofibroblasts is to repair tissue by depositing extracellular matrix and contracting tissue, as in wound closing. Fibrotic diseases, including IPF, arise from dysregulated wound remodeling involving chronic matrix deposition and tissue contraction long after initial tissue trauma has been resolved. The herein disclosed methods and compositions treat fibrotic disease by inhibiting the Hh signaling pathway so that upregulated hedgehog can no longer drive this pathology, blocking the generation of myofibroblasts and stopping the chronic remodeling that causes fibrosis. Although this mechanism has been clinically validated, the promise of Hh pathway inhibitors to treat fibrosis has so far not been realized.

It is disclosed herein that certain 1,4-disubstituted phthalizines that are potent inhibitors of SMO and the downstream transcription factors Gli1 and Gli2, and that exhibit a desirable toxicology profile, fulfill this promise. The present embodiments provide methods of treatment using compounds of Formula I:

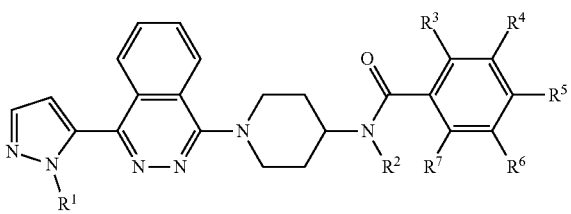

wherein, $R^1$ is hydrogen or methyl; $R^2$ is hydrogen or methyl; $R^3$, $R^4$, $R^5$, $R^6$, or $R^7$ are independently hydrogen, fluoro, chloro, cyano, trifluoromethyl, trifluoromethoxy, difluoromethoxy, methylsulfonyl, or trifluoromethylsulfonyl, provided that at least three of $R^3$, $R^4$, $R^5$, $R^6$, and $R^7$ are hydrogen; or a pharmaceutically acceptable salt thereof. Under standard nomenclature used throughout this disclosure, the terminal portion of the designated side chain is described first, followed by the adjacent functionality toward the point of attachment. For example, a methylsulfonyl substituent is equivalent to $CH_3—SO_2—$. "Pharmaceutically acceptable salts" refers to the relatively non-toxic, inorganic and organic salts of compounds of the present invention.

Compounds of Formula I and their synthesis are described in U.S. Pat. No. 9,000,023, which is hereby incorporated by reference in its entirety.

The present embodiments also provide a pharmaceutical composition comprising a compound of Formula I, or a pharmaceutically acceptable salt thereof, in combination with a pharmaceutically acceptable excipient, carrier or diluent for use in the methods of treatment. A "pharmaceutically acceptable carrier, diluent, or excipient" is a medium generally accepted in the art for the delivery of biologically active agents to mammals, e.g., humans.

A paradigmatic compound of Formula I is 4-Fluoro-N-methyl-N-(1-(4-(1-methyl-1H-pyrazol-5-yl)phthalazin-1-yl)piperidin-4-yl)-2-(trifluoromethyl)benzamide (CAS 1258861-20-9):

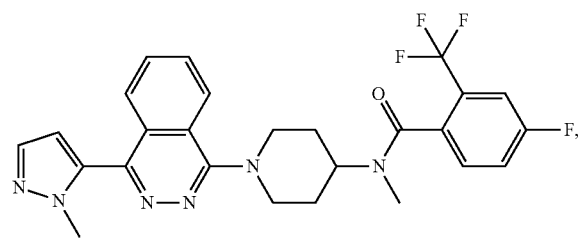 [SMILES: CN(C(=O)c1ccc(F)cc1C(F)(F)F)C1CCN(c2nnc(-c3ccnn3C)c3ccccc23)CC1]

also known as taladegib. Taladegib (also referred to as LY2940680) is a potent, selective, and orally available Smo inhibitor with a favorable safety profile, capable of disrupting the Hh pathway. This molecule has been in over 192 human subjects and developed initially with the intention of treating oncologic indications with a focus on lung cancer and basal cell carcinoma (BCC). Although primarily cancer patients, these studies allowed for a preliminary understanding of dose and tolerability. Taladegib is orally bioavailable. In some embodiments, the mean oral bioavailability is from about 72% to about 91%.

The major metabolite of taladegib, M75, an oxidative N-desmethylation product, retains activity as an inhibitor of SMO. M75 is understood to have lost the methyl group at $R^2$ of Formula I, so that position is hydrogen instead of methyl.

Taladegib is well-suited to target the lung compared to vismodegib. In animal models, taladegib is greater than 20-fold more potent than vismodegib at inhibiting Gli1 in the lungs, a downstream effector molecule that is expressed when the Hh pathway is activated. The clinically established MTD for taladegib is 400 mg. At this dose, Gli1 mRNA inhibition is >85% in skin with a discontinuation of approximately 9%. Taladegib has been evaluated clinically at a dose as low as 50 mg (i.e., 8-fold lower than the clinically established MTD) where inhibition of Gli1 mRNA was still greater than 80%. In contrast, vismodegib inhibits Gli1 mRNA less than 50% at its MTD of 150 mg. Taladegib has a better clinical safety profile than vismodegib, with substantially lower occurrence of muscle spasms (40% versus up to 80%). Thus, while vismodegib proved unsuitable for IPF, clinical studies with vismodegib indicated inhibition of the Hh pathway can improve lung function in IPF patients.

Compounds of Formula I inhibit Gli1 activity, generally with an $IC_{50}$ of <40 nM, as measured in Daoy cells and described in U.S. Pat. No. 9,000,023. Taladegib has an $IC_{50}$ of about 2.4 nM in this assay. Such compounds constitute means for inhibiting Gli1 activity or means for inhibiting SMO.

Additionally, U.S. Patent Application Publication No. 20200000784 A1 is incorporated herein by reference for all that it teaches about the use of taladegib for the treatment of fibrosis, particularly idiopathic pulmonary fibrosis.

Certain analogues of the above phthalazines are potent inhibitors of SMO and the downstream transcription factors Gli1 and Gli2, and that exhibit a desirable toxicology profile. In some embodiments, the inhibitor of SMO, the inhibitor of Gli1, or the means for inhibiting Gli1 or SMO is a compound of Formula II:

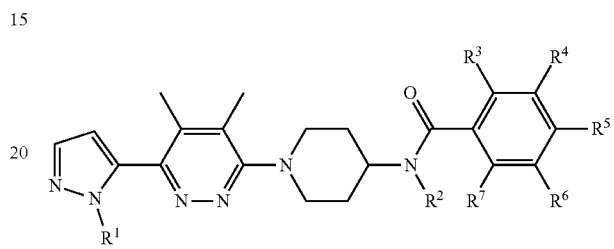

wherein, $R^1$ is hydrogen or methyl; $R^2$ is hydrogen or methyl; $R^3$, $R^4$, $R^5$, $R^6$, or $R^7$ are independently hydrogen, fluoro, chloro, cyano, trifluoromethyl, trifluoromethoxy, difluoromethoxy, methylsulfonyl, or trifluoromethylsulfonyl, provided that at least three of $R^3$, $R^4$, $R^5$, $R^6$, and $R^7$ are hydrogen; or a pharmaceutically acceptable salt thereof. In some embodiments, the compound of Formula II is N-(1-(4,5-dimethyl-6-(1-methyl-1H-pyrazol-5-yl)pyridazin-3-yl)piperidin-4-yl)-4-fluoro-2-(trifluoromethyl)benzamide, having the structure

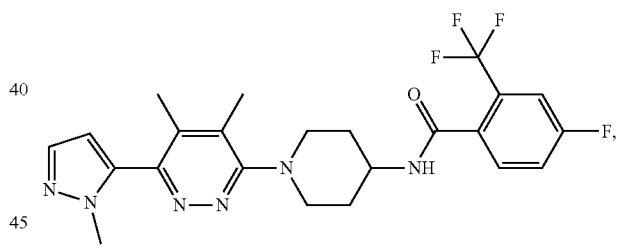

also known as L-4.

L-4 is described in Zhu et al., (*L-4, a Well-Tolerated and Orally Active Inhibitor of Hedgehog Pathway, Exhibited Potent Anti-tumor Effects Against Medulloblastoma* in vitro and in vivo, Frontiers in Pharmacology 10:89, 2019), which is hereby incorporated by reference in its entirety. Zhu et al. describe L-4 as a promising anti-cancer agent. It is reported to have a similar $ID_{50}$ for Hh inhibition as taladegib, 2.33 nM versus 2.26 nM, respectively.

Like taladegib and compounds of Formula I, L-4 and compounds of Formula II constitute means for means for inhibiting Gli1 activity or means for inhibiting SMO. Various embodiments specifically exclude compounds of Formula I, compounds of Formula II, or particular sub-genera or species of Formula I or Formula II.

The compounds of the present invention are capable of reaction, for example, with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," Journal of Pharmaceutical Sciences, Vol 66, No. 1, January 1977.

The herein disclosed compounds can be formulated as pharmaceutical compositions using a pharmaceutically acceptable carrier, diluent, or excipient and administered by a variety of routes. In particular embodiments, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19.sup.th ed., Mack Publishing Co., 1995).

In some embodiments, the herein disclosed compounds of can be formulated as tablets containing 50 or 100 mg of the compound and the common pharmaceutical ingredients: croscarmellose sodium, HPMCAS-H, mannitol, microcrystalline cellulose, silicon dioxide, and sodium stearyl fumarate. One particular embodiment contains 16.1% taladegib, 37.6% HPMCAS-H, 9.3% mannitol, 28.6% microcrystalline cellulose, 2.9% croscarmellose sodium, 1.0% silicon dioxide, 1.2% sodium stearyl fumarate, and 3.4% Opadry (Film Coating).

IPF is a dysregulated wound healing process causing progressive fibrotic lung scarring. Targeting the Hedgehog pathway is a logical therapeutic approach to slow, halt or reverse progression of the disease. In wound healing processes, the Hh pathway regulates the activation of fibroblasts and transdifferentiation into myofibroblasts which when dysregulated become key drivers of fibrosis. In IPF myofibroblasts infiltrate the lung where they produce extracellular matrix proteins such as collagen. The myofibroblasts adhere to the extracellular matrix and pull the lung closed similar to pulling a wound closed. The result of the myofibroblast activity is progressive loss of lung function through fibrosis and tissue remodeling.

Targeting the Hh pathway via Smo inhibition has been validated both clinically and preclinically. In a clinical setting, the FDA-approved Smo inhibitor, vismodegib (approved as Erivedge® for treatment of adults with metastatic BCC or locally advanced BCC), was evaluated in a single arm IPF study in combination with pirfenidone. After six months of treatment, patients on average demonstrated an increase in Forced Vital Capacity (FVC) of approximately 100 mL. Increased FVC and lung capacity have not been seen in previous clinical studies interrogating any other target considered for IPF. While Smo inhibition to disrupt the Hh pathway as a therapeutic target for IPF was validated, vismodegib was poorly tolerated by patients, as severe muscle spasms were a significant adverse event resulting in discontinuation of over 40% of participants. This discontinuation rate is similar to the discontinuation rate experienced by patients with BCC taking vismodegib. All further development for vismodegib as an IPF therapeutic was discontinued.

Inhibition of Gli1 mRNA in skin is similar to inhibition of Gli1 mRNA in the lungs. Gli1 mRNA inhibition in skin biopsies has been measured as a surrogate for Gli1 mRNA inhibition in lungs in clinical studies of lung cancer. Nonclinical in vivo models demonstrated that the kinetics and magnitude of Gli1 mRNA inhibition by orally administered taladegib were very similar in the skin and lungs of mice. Additionally, the extent of Gli1 mRNA inhibition in the skin and lungs of mice was similar to the extent of Gli1 mRNA inhibition observed in the skin biopsies of human subjects being treated with clinically relevant doses.

IPF patient samples have shown increased levels of Hh pathway components and myofibroblasts. Several studies examined tissues from IPF patient lung samples and compared them to lung samples of healthy subjects. It was clear there is a significant increase in SHh (the activating ligand of the Hh pathway) and Gli1. Normal lungs did not present with any detectable amount of either SHh or Gli1, but IPF samples stained very strongly indicating a significant presence. IPF lung samples also stained very strongly for α-Smooth Muscle Actin 1 (α-SMA1) which is a marker that defines myofibroblasts. Normal healthy lung samples had little to no staining of α-SMA1.

Hh pathway disruption to inhibit fibrosis has been demonstrated in vitro and in a number of animal models using several Smo inhibitors. These animal models have similar features that capitulate fibroblast infiltration and transdifferentiation into myofibroblasts that then drive progressive fibrosis. Inhibition of Smo was observed to disrupt fibrosis and in some cases reverse the disease. Additionally, it has been demonstrated that inhibition of Smo resulted in increased apoptosis of infiltrated myofibroblasts, reduction of α-SMA1, reduction of Gli1 and SHh, and reduction of collagen.

Nonclinical toxicity findings for taladegib are similar to approved drugs in this class, with the important potential risks associated with on target effects of taladegib considered to be hepatic injury, effects on the reproductive organs, rhabdomyolysis, reproductive toxicity and bone effects. Class effects not yet observed with taladegib, clinically or nonclinically, include amenorrhea.

Clinically, the mean half-life ($t_{1/2}$) across all doses was estimated to be approximately 16 hours for taladegib, allowing for once daily dosing. Median $t_{max}$ was 2 hours.

Taladegib has demonstrated a favorable safety profile in 6 industry-sponsored studies that have been conducted, primarily in advanced cancer patients. As a monotherapy in advanced cancer, the most commonly observed adverse events (AEs) were nausea, diarrhea, dysgeusia, fatigue, decreased appetite, alopecia, vomiting, muscle spasm, constipation, weight decrease, and headache.

The relationship between the efficacy and toxicity of a drug is generally expressed in terms of therapeutic window and therapeutic index. Therapeutic window is the dose range from the lowest dose that exhibits a detectable therapeutic effect up to the maximum tolerated dose (MTD); the highest dose that will the desired therapeutic effect without producing unacceptable toxicity. Most typically therapeutic index is calculated as the ratio of $LD_{50}:ED_{50}$ when based on animal studies and $TD_{50}:ED_{50}$ when based on studies in humans (though this calculation could also be derived from animal studies and is sometime called the protective index), where $LD_{50}$, $TD_{50}$, and $ED_{50}$ are the doses that are lethal, toxic, and effective in 50% of the tested population, respectively.

In various aspects of these embodiments the toxicity is an observable toxicity, a substantial toxicity, a severe toxicity, or an acceptable toxicity, or a dose-limiting toxicity (such as but not limited to a MTD). By an observable toxicity it is meant that while a change is observed the effect is negligible or mild. By substantial toxicity it is meant that there is a negative impact on the patient's overall health or quality of life. In some instances a substantial toxicity may be mitigated or resolved with other ongoing medical intervention. By a severe toxicity it is meant that the effect requires acute medical intervention and/or dose reduction or suspension of treatment. The acceptability of the toxicity will be influenced by the particular disease being treated and its severity and the availability of mitigating medical intervention.

Toxicities and adverse events are sometimes graded according to a 5 point scale. A grade 1 or mild toxicity is asymptomatic or induces only mild symptoms; may be characterized by clinical or diagnostic observations only; and intervention is not indicated. A grade 2 or moderate toxicity may impair activities of daily living (such as preparing meals, shopping, managing money, using the telephone, etc.) but only minimal, local, or non-invasive interventions are indicated. Grade 3 toxicities are medically significant but not immediately life-threatening; hospitalization or prolongation of hospitalization is indicated; activities of daily living related to self-care (such as bathing, dressing and undressing, feeding oneself, using the toilet, taking medications, and not being bedridden) may be impaired. Grade 4 toxicities are life-threatening and urgent intervention is indicated. Grade 5 toxicity produces an adverse event-related death. Thus, in various embodiments, use of a drug in the herein disclosed regimen or dosage reduces the grade of a toxicity associated with treatment by at least one grade as compared to use of that drug according to another regimen. In other embodiments, by use of a drug according to a specified regimen or dosage, a toxicity is confined to grade 2 or less, grade 1 or less, or produces no observation of the toxicity. In some embodiments, a therapeutic index of a herein disclosed inhibitor of Gli1 or SMO is greater than that of vismodegib (approximately 0.37). In comparison, the therapeutic of taladegib is approximately 8. In some embodiments, a therapeutic index of a herein disclosed inhibitor of Gli1 or SMO is greater than 1, 2, 3, 4, 5, 6, or 7.

Aspects of the present specification provide, in part, administering an effective amount (or therapeutically effective amount) of a compound or a composition disclosed herein. As used herein, the term "effective amount" is synonymous with "effective dose" and when used in reference to treating IPF means at least the minimum dose of a compound or composition disclosed herein necessary to achieve the desired therapeutic effect. An effective dosage or amount of a compound or a composition disclosed herein can readily be determined by the person of ordinary skill in the art considering all criteria (for example, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof) and utilizing his best judgment on the individual's behalf, especially in light of the exemplary dosages and other information disclosed herein. In some embodiments, an effective dose is 25, 50, 75, 100, 150, 200, 250, 300, 350, or 400 mg, or falls in a range bound by any pair of the preceding values. In some embodiments, the effective dose is administered once a day.

In some embodiments, the dosage of taladegib, L-4, or related compounds, is begun at 200 mg/day. In some embodiments, the dosage is provided in a single daily dose. If grade 3 or higher AEs are observed, dosing is stepped down. In some embodiments, the dosage is stepped down in decrements of 50 mg/day as needed to avoid grade 3 or higher AEs, to as little as 50 mg/day. In some embodiments, an initial dosage (before step-down) can be any dosage higher than the lowest dosage deemed an effective dose. In some embodiments, the initial dosage in is the top half of the effective dose range. In some embodiments, the initial dosage is at the top of the effective dose range. For example, if the effective dose range in 50-200 mg, an initial dose could be >50 mg (e.g., 75 mg), 125-200 mg, or 200 mg. In some instances, the initial dosage is in a range of 100-300 mg/day. In some instances, the step-down in dosage is 25, 50, or 100 mg/day.

In some embodiments, an effective dose of the inhibitor of Gli1 or SMO, or means for inhibiting Gli1 or SMO results in stabilization or improvement of fibrosis, such as with respect to the physical extent of fibrosis, lung function, or other measure as described herein. In further embodiments, the stabilization or improvement of fibrosis is achieved without the patient experiencing drug-related adverse events (toxicities). In particular instances, the avoided drug-related adverse events are grade 3 or higher toxicities. In some embodiments, the absent drug-related adverse events are muscle spasms, QT elongation or a liver toxicity.

Various aspects are methods of treating fibrosis by administering an inhibitor of Gli1 or SMO, or means for inhibiting Gli1 or SMO, to a patient in need thereof, that is, a patient having a fibrotic disease. In some embodiments, the inhibitor of Gli1 or SMO, or means for inhibiting Gli1 or SMO is used as monotherapy. In some embodiments, the inhibitor of Gli1 or SMO, or means for inhibiting Gli1 or SMO is used in combination with another anti-fibrosis drug. In some embodiments, the other anti-fibrosis drug is not a Hh pathway inhibitor. In some instance the non-Hh pathway inhibitor anti-fibrosis drug is pirfenidone, nintedanib, GLPG4716 or PRM-151.

In some embodiments, the fibrotic disease is idiopathic pulmonary fibrosis (IPF). In some embodiments, the fibrotic disease is pulmonary fibrosis following infection, including a bacterial or viral infection. In most instances, the fibrosis develops after years-long chronic infections so that the role of the infection in causing the fibrosis cannot be conclusively demonstrated; such fibrosis is therefore still classified as idiopathic. Covid-19 provides a counterpoint, in that onset of fibrosis can be very rapid. In some embodiments, the pulmonary fibrosis follows infection with SARS-CoV-2. In some embodiments, the fibrotic disease is scleroderma. In some instances, the fibrotic disease is systemic scleroderma (also known as systemic sclerosis) and in further instances, systemic scleroderma involving the lung. In some embodiments, the fibrotic disease is liver fibrosis, such as in non-alcoholic steatohepatitis (NASH). In some embodiments, the fibrotic disease is kidney fibrosis, for example, renal interstitial fibrosis or renal allograft fibrosis. In some embodiments, the fibrotic disease is gastric fibrosis, for example, gastric mucosal fibrosis, glandular stomach fibrosis, or retroperitoneal fibrosis. In some embodiments, the patient is a human. In some embodiments, the patient is a non-human animal, for example a mammal.

For each method of treatment, there are parallel embodiments expressed as use of the inhibitor of Gli1 or SMO, or the means for inhibiting Gli1 or SMO, in the treatment of a fibrotic disease, or their use in the manufacture of a medicament for the treatment of a fibrotic disease, or a composition or pharmaceutical composition for use in treating a fibrotic disease, and the like.

The terms "treatment" "treating", etc., refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. Various embodiments may specifically include or exclude one or more of these modes of treatment.

Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like, that are then acted upon by any other person including other healthcare professionals or the patient him/herself. This includes, for example, direction to the patient to undergo, or to a clinical laboratory to perform, a diagnostic procedure, such as imaging or an evaluation of lung function, so that ultimately the patient may receive the benefit appropriate treatment. In some embodiments, the orders, instructions, and advice aspect of treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like. All such orders, instructions, and advice are to be seen as conditioning receipt of the benefit of the treatment on compliance with the instruction. In some instances, a financial benefit is also received by the patient for compliance with such orders, instructions, or advice. In some instances, a financial benefit is also received by the healthcare professional for compliance with such orders, instructions, or advice.

Treatment efficacy or benefit for pulmonary fibrosis is commonly assessed by changes in lung function for example, as determined by spirometry. Spirometry measures that can be used include forced vital capacity (FVC), forced expiratory volume in 1 second ($FEV_1$), and diffusion capacity of the lungs for carbon monoxide ($DL_{CO}$). Further spirometry parameters that can be considered include $FEV_1$/FVC ratio, observed FVC as a percentage of predicted FVC (FVC % predicted), and observed $FEV_1$ as a percentage of predicted $FEV_1$ ($FEV_1$% predicted). The predicted value of FVC (in liters) as published by the Association for Respiratory Technology and Physiology is 5.76*height (in meters)−0.026*age (in years)−4.34. The predicted value of $FEV_1$ (in liters) as published by the Association for Respiratory Technology and Physiology is 4.30*height (in meters)−0.029*age (in years)−2.49.

Other assessments include:
appearance of the lungs—quantitative extent of fibrosis (including scarring or remodeling), by percent and/or volume, as determined by CT scan, magnetic resonance imaging (MRI), and the like;
appearance of the lungs—qualitative extent of fibrosis: improved, same, or worse), as determined by CT scan, magnetic resonance imaging (MRI), and the like;
the number of respiratory hospitalizations;
the distance that can be walked in a set interval of time, for example, 6-minute walk distance; and
scores on a respiratory health questionnaire, for example, St. George's Respiratory Questionnaire, the UCSD Shortness of Breath Questionnaire, and the like.

Assessments.

The spirometry and other assessments may be made at regular intervals, for example, about every 24 weeks, quarterly, semi-annually, or annually.

Treatment efficacy or benefit may be observed as a decrease in the progression of the disease, a stabilization of the disease, or improvement in the patient's condition. In some embodiments, progression, stabilization, or improvement is judged in comparison to a previous measurement or measurements of that patient. In some embodiments, the previous measurement is a baseline measurement prior to initiation of treatment. In some embodiments, progression, stabilization, or improvement is judged based in comparison with other patients, actual or historical, receiving no treatment, placebo, or alternative treatment. Thus, in some embodiments, improvement or stabilization is judged by comparison to what would be expected in an untreated patient. For example, in such embodiments, decreased scarring includes an increase in scarring that is less than would be expected in an untreated patient. Thus a stabilization of lung function does not imply no further decrease in one or another measure of lung function but rather that any decrease does not exceed that expected with aging for the time interval considered.

EXAMPLES

The following non-limiting examples are provided for illustrative purposes only in order to facilitate a more complete understanding of representative embodiments now contemplated. These examples should not be construed to limit any of the embodiments described in the present specification, Example 1

In Vitro Pharmacology of Taladegib

Using an in vitro competitive binding assay, half-maximal inhibitory concentration ($IC_{50}$) and binding constant ($K_i$) were calculated based on the competitive displacement of a radioligand. Taladegib binds to hSMO receptor and inhibits binding of $^3$H-2406189 (a known hSMO agonist) to hSMO, with $K_i$ of 76.4±75.3 nM and $IC_{50}$ of 144±143 nM (n=4, geometric mean±standard error [SE]).

To determine the biological activity of taladegib in mouse cells, Gli-Luciferase activity was quantified in a mouse mesenchymal C3H10T½ cell line stimulated with sonic hedgehog conditioned media (SHh-CM). Taladegib hydrochloride inhibited Hh signaling activity in mouse C3H10T½ cells with an $IC_{50}$ of 11.2±5.33 nM (n=8, geometric mean±SE). To determine the biological activity of taladegib in human cells, Gli1 transcript levels were quantified in a human Daoy tumor cell line stimulated with SHh-CM. Taladegib hydrochloride inhibited Hh signaling activity in human Daoy cells with an $IC_{50}$ of 2.22±1.14 nM as determined by measurement of Gli1 mRNA using branched chain deoxyribonucleic acid (DNA) assay technology (n=8, geometric mean±SE).

Example 2

In Vivo Pharmacology of Taladegib

In order to understand PK/PD effects and to guide the dosing regimen for efficacy studies, key PK/PD studies involving dose response and time course were carried out following a single oral administration of the taladegib in Balb/c surrogate and $PTCH^{-/+}xp53^{-/-}$ tumor models. Following the predetermined dosing period, surrogate tissues (lung, skin, and cerebellum) from Balb/C mouse and tumor from $Ptch^{-/+}xp53^{-/-}$ transgenic tumor model were harvested, processed, and evaluated for Gli1 expression levels using a quantitative reverse transcription polymerase chain reaction TaqMan® assay. As summarized in Table 1, taladegib inhibited Hh signaling as measured by mouse Gli1 expression levels in tissues evaluated. The time course study demonstrated that sustained target inhibition can be maintained for at least 24 hours following a single oral dose of taladegib hydrochloride at 8 mg/kg. Given the parallel PD effects, skin Gli1 is an appropriate PD surrogate for lung tissue Gli1.

TABLE 1

Summary Table of $TED_{50}$ and $TEC_{50}$ of Taladegib Hydrochloride in Mouse Pharmacodynamic Models

| Mouse | Lung mGli1 | | Skin mGli1 | | Cerebellum mGli1 | | Brain Tumor mGli1 | |
|---|---|---|---|---|---|---|---|---|
| | $TED_{50}$ (mg/kg) | $TEC_{50}$ (ng/ml) | $TED_{50}$ (mg/kg) | $TEC_{50}$ (ng/ml) | $TED_{50}$ (mg/kg) | $TEC_{50}$ (ng/ml) | $TED_{50}$ (mg/kg) | $TEC_{50}$ (ng/ml) |
| Balb/c | 2.6 ± 0.6 | 264 ± 114 | 1.1 | 84 | 2.2 | 230 | — | — |
| PTCH Tg | — | — | — | — | — | — | 1.0 | 63.0 |

Abbreviations:
SE = standard error;
$TEC_{50}$ = threshold effective concentration;
$TED_{50}$ = threshold effective dose;
Tg = transgenic.

Example 3

SMO Inhibitor Improves FVC in IPF Patients

The results of various clinical trials of treatments for IPF were compared (FIG. 1). Whereas the anti-inflammatory pirfenidone, and the kinase inhibitor nintedanib, were only able to slow the deterioration of FVC, the SMO inhibitor vismodegib (in combination with pirfenidone) was able to produce a substantial increase in FVC, suggesting a reversal of pathology. The autotaxin inhibitor zirtaxestat (also known as GLPG1690) produced a small increase in FVC in a Phase 1b trial, however development of this drug was abandoned during a phase 3 trial due to a risk-benefit profile that in the assessment of an Independent Data Monitoring Committee no longer supported its use. All development of ziraxestat has been discontinued. Development of vismodegib was also discontinued for IPF treatment due to severe muscle spasms, but these data validate the use of Hh inhibitors in the treatment of IPF.

Example 4

Figure 2:
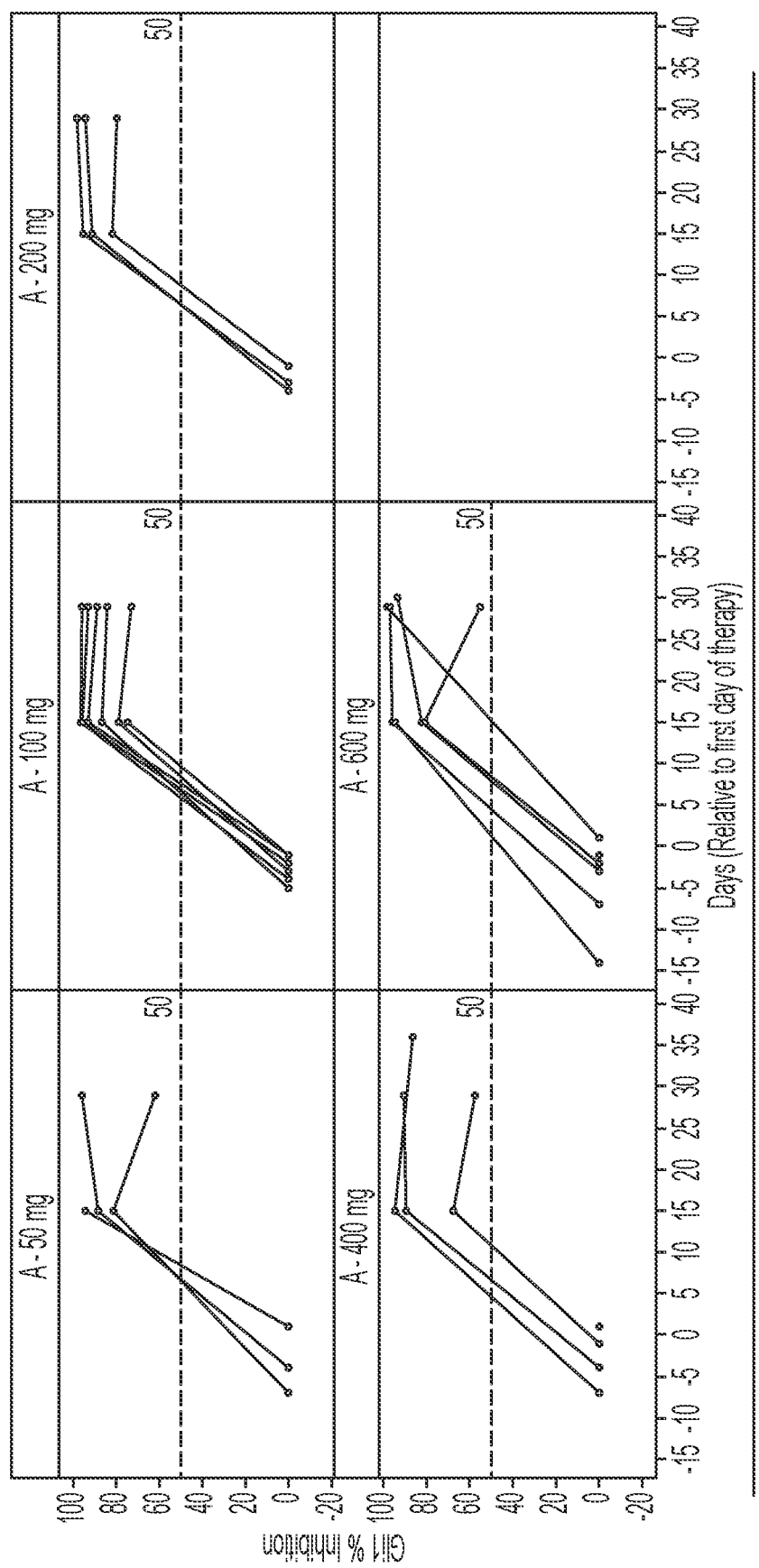
FIG. 2 depicts Gli1 mRNA inhibition (%) in skin samples from patients receiving various doses of taladegib.

Lower Doses of Taladegib Reduce Severity of Muscle Spasm Adverse Events but Maintain Degree of Gli1 Inhibition Taldegib was administered to subjects at doses of 50, 100, 200, 400 and 600 mg. At these doses most patients exhibited >80% inhibition of Gli as measured in skin biopsies (FIG. 2). While some grade 3 toxicities were seen at 400 mg/day, there were none at 200 or 100 mg/day (Table 2). Given that the minimal biological effective dose (BED) was defined in this study as the first dose level at which the inhibition of mGli1 was >50%, it was concluded that taladegib was pharmacologically active at all dose levels tested.

TABLE 2

Dose-Muscle Spasm AE Correlation

| | Muscle Spasm Adverse Event Frequency Reported | | | |
|---|---|---|---|---|
| Dose level (n patients) | Grade 1 (n patients) | Grade 2 (n patients) | Grade 3 (n patients) | Grade 4 (n patients) |
| 100 mg (24) [T] | 21% (5) | 0 | 0 | 0 |
| 200 mg (12) [T] | 17% (2) | 17% (2) | 0 | 0 |

TABLE 2-continued

Dose-Muscle Spasm AE Correlation

| | Muscle Spasm Adverse Event Frequency Reported | | | |
|---|---|---|---|---|
| Dose level (n patients) | Grade 1 (n patients) | Grade 2 (n patients) | Grade 3 (n patients) | Grade 4 (n patients) |
| 400 mg (90) [T] | 17% (15) | 10% (9) | 4% (4) | 0 |
| 150 (104) [V] | 43% (45) | 22% (23) | 6% (7) | 0 |

AE data collected from multiple clinical trials including a phase 1b trial for combination with etoposide and carboplatin. Dose levels with less than 10 patients excluded due to insufficient power.
[T] taladegib
[V] vismodegib

Example 5

Comparison of Predominant AEs for Drugs Tested for IPF Treatment

Figure 3:
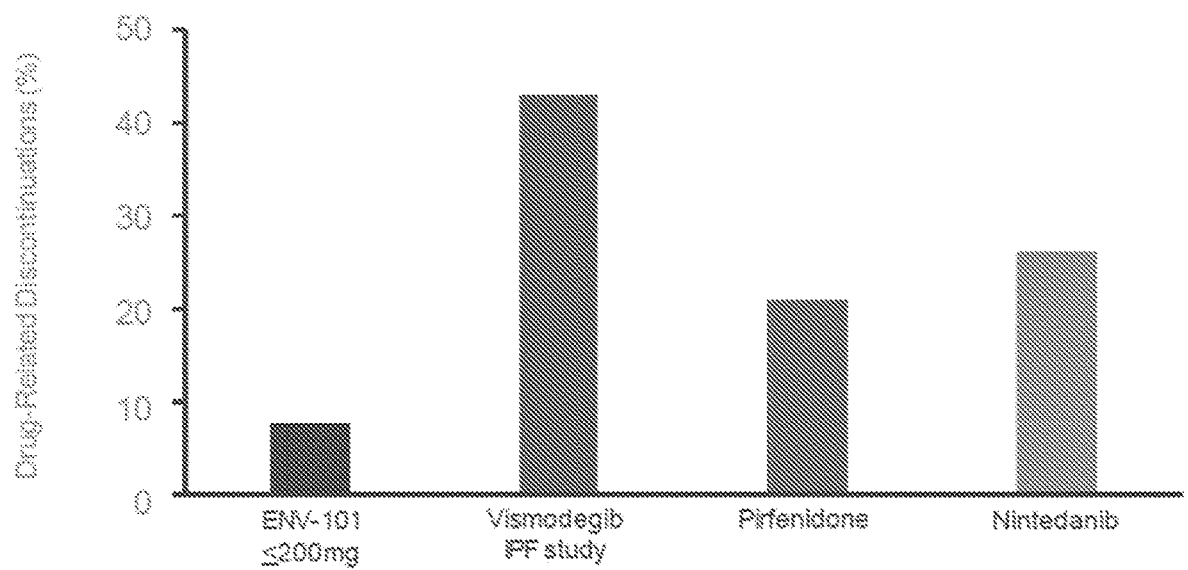
FIG. 3 depicts the rate of drug-related discontinuations in clinical trials for four drugs considered for IPF treatment.

Taladegib, vismodegib, pirfenidone, and nintedanib have all been used in clinical trials and have been used or evaluated for use in treating IPF. Except for taladegib, >20% of patients discontinued treatment for drug related reasons (FIG. 3). The predominant AE causing discontinuation was muscle spasms for vismodegib, nausea for pirfenodone, and diarrhea for nintedanib. There was no prevalent AE for taladegib and <10% patients discontinued treatment for drug related reasons when the dosage was ≤200 mg/day.

Example 6

Reduction of Myofibroblasts in Bleomycin-Induced Pulmonary Fibrosis Model

The Bleomycin (BLM) induced pulmonary fibrosis model is a standard IPF model, widely used in pharmacology and fundamental research. The disease IPF is defined as injury confined to the lungs that is progressive and irreversible. In IPF patients, loss of lung function is driven by the infiltration and expansion of activated myofibroblasts. A Microsprayer® Aerosolizer was used to perform intratracheal administration of bleomycin. By administering bleomycin via Microsprayer® Aerosolizer, it can be evenly exposed to the lungs and thus, develops a reproducible and uniform pathology. In this model, the presence of myofibroblasts are observed by immunohistochemistry when stained with anti-alpha-smooth muscle actin ($\alpha$-SMA) antibodies.

Figure 4A:
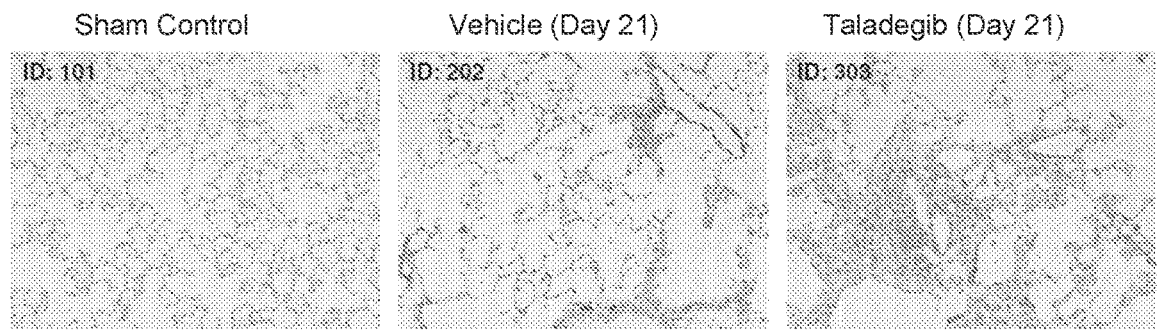
FIGS. 4A-B portray α-SMA protein levels with and without taladegib treatment in a bleomycin-induced pulmonary fibrosis model.
Figure 4B:
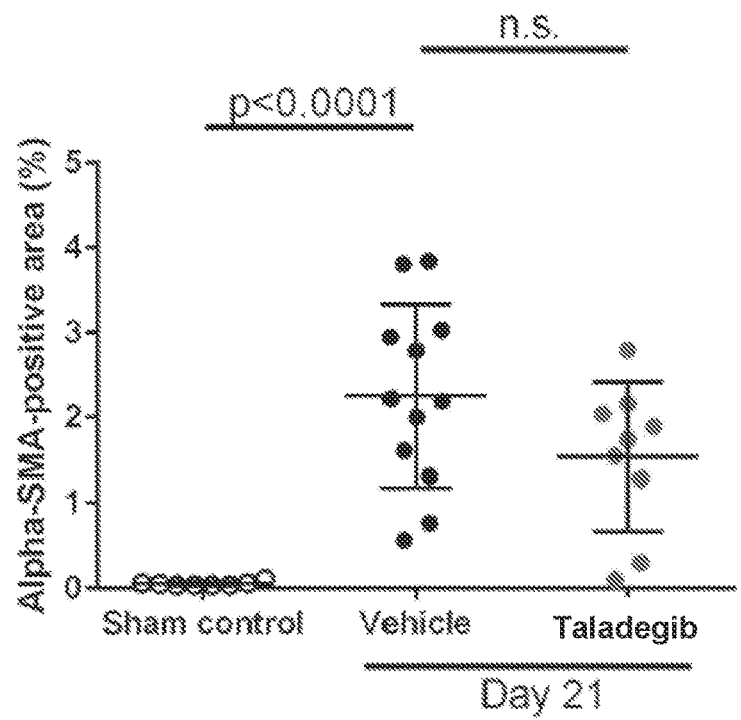

Animals were exposed to bleomycin and then treated with taladegib at the onset of fibrosis on day seven. Pathology of animals was examined on day 21 of the study. Treatment with taladegib at 5 mg/kg orally administered daily resulted in approximately 40% reduction of $\alpha$-SMA protein expression indicating a reduction of myofibroblasts (FIGS. 4A-B).

Example 7

A Phase 2, Multi-Center Study Evaluating the Safety and Efficacy of Taladegib in Subjects with IPF Patients diagnosed with IPF based upon American Thoracic Association, Japanese Respiratory Society, European Respiratory Society, Latin American Thoracic Association guidelines, and confirmed by high resolution computed tomography (HRCT), having percent predicted FVC of >50% and percent predicted $DL_{CO}$ between 35% and 85%, are randomized in to taladegib and placebo groups. Baseline results from lung function tests (FVC, $FEV_1$ and $DL_{CO}$), HRCT, and the UCSD Shortness of Breath (SOB) questionnaire are obtained. Taladegib is administered daily for 12 weeks, starting at 200 mg/day. The patients are observed an additional 6 weeks after the scheduled treatment is completed. If medication-related adverse events are experienced, the dosage may be reduced to as little as 100 mg/day. Lung function tests and the UCSD SOB questionnaire are administered again at weeks 6, 12, and 18 of the study. HRCT is repeated at 12 weeks. Efficacy is assessed by change from baseline for FVC, $FEV_1$, $FEV_1$/FVC ratio, FVC % predicted, $FEV_1$% predicted, and $DL_{CO}$ and the UCSD SOB questionnaire at weeks 6, 12, and 18. Quantitative (% and mL) and qualitative (improved, same, worse) assessment of lung fibrosis by HRCT will be performed at Screening and Week 12. The Screening HRCT will serve as the baseline for study HRCT assessments. At 12 weeks, no or limited dose limiting toxicities are observed. At 12 weeks, some efficacy endpoints demonstrate stabilization or improvement. At 18 weeks, durability of the response is observed. Patients did not experience serious drug-related adverse events (after sufficient step-down of dosage, if any), including the absence of muscle spasms.

Example 8

Covid-19 Therapy Clinical Trial

Patients recovered from SARS-CoV-2 infection showing lung fibrosis by CT scan are randomized for treatment with standard of care or taladegib monotherapy. Taladegib is administered daily starting at 200 mg. If medication-related adverse events are experienced, the dosage may be reduced in steps of 100 mg to reduce or eliminate adverse events. Phamacokinetic data is collected. The primary efficacy endpoint is FVC change from baseline at 24 weeks. Secondary efficacy endpoints are change in lung fibrosis from baseline CT scan, change from baseline in 6-minute walk distance, the number of adjudicated respiratory hospitalizations, and change from baseline in St. George's Respiratory Questionnaire. At 24 weeks some efficacy endpoints demonstrate stabilization or improvement. Patients did not experience serious drug-related adverse events (after sufficient step-down of dosage, if any), including the absence of muscle spams.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A pharmaceutical composition comprising HPMCAS-H, mannitol, microcrystalline cellulose, croscarmellose sodium, silicon dioxide, sodium stearyl fumarate, and taladegib, or a pharmaceutically acceptable salt thereof.

2. The pharmaceutical composition of claim 1, comprising 14.5-17.7% taladegib.

3. The pharmaceutical composition of claim 1, comprising 14.5-17.7% taladegib and 33.9-41.4% HPMCAS-H.

4. The pharmaceutical composition of claim 1, comprising 14.5-17.7% taladegib, 33.9-41.4% HPMCAS-H, and 8.4-10.2% mannitol.

5. The pharmaceutical composition of claim 1, comprising 14.5-17.7% taladegib, 33.9-41.4% HPMCAS-H, 8.4-10.2% mannitol, 25.7-31.5% microcrystalline cellulose, and 2.6-3.2% croscarmellose sodium.

6. The pharmaceutical composition of claim 1, comprising 14.5-17.7% taladegib, 33.9-41.4% HPMCAS-H, 8.4-10.2% mannitol, 25.7-31.5% microcrystalline cellulose, 2.6-3.2% croscarmellose sodium, and 0.9-1.1% silicon dioxide.

7. The pharmaceutical composition of claim 1, comprising 14.5-17.7% taladegib, 33.9-41.4% HPMCAS-H, 8.4-10.2% mannitol, 25.7-31.5% microcrystalline cellulose, 2.6-3.2% croscarmellose sodium, 0.9-1.1% silicon dioxide, and 1.1-1.3% sodium stearyl fumarate.

8. The composition of claim 1 wherein said composition is in a tablet form.

9. The composition of claim 8, wherein said tablet comprises 50 mg of taladegib.

10. The composition of claim 8, wherein said tablet comprises 100 mg of taladegib.

11. The composition of claim 3, wherein said composition is in a tablet form.

12. The composition of claim 11, wherein said tablet comprises 50 mg of taladegib.

13. The composition of claim 11, wherein said tablet comprises 100 mg of taladegib.

* * * * *